United States Patent [19]

Mushika

[11] Patent Number: 4,796,606

[45] Date of Patent: Jan. 10, 1989

[54] DRIVE UNIT FOR MEDICAL PUMP

[75] Inventor: Sadahiko Mushika, Tokyo, Japan

[73] Assignee: Aisin Seiki Kabushiki Kaisha, Kariya, Japan

[21] Appl. No.: 89,792

[22] Filed: Aug. 27, 1987

[30] Foreign Application Priority Data

Aug. 27, 1986 [JP] Japan .................................. 61-201091

[51] Int. Cl.$^4$ ............................................ A61B 19/00
[52] U.S. Cl. ............................................. 600/18; 623/3
[58] Field of Search ................... 128/1 D, DIG. 3; 604/4–6; 623/3

[56] References Cited

U.S. PATENT DOCUMENTS

| | | | |
|---|---|---|---|
| 4,462,355 | 7/1984 | Pieronne et al. | 128/1 D |
| 4,516,567 | 5/1985 | Veragen | 128/1 D |
| 4,522,194 | 6/1985 | Normann | 128/1 D |
| 4,524,466 | 6/1985 | Hall et al. | 128/1 X |
| 4,648,385 | 3/1987 | Ovin et al. | 128/1 D |

FOREIGN PATENT DOCUMENTS

736980 6/1980 U.S.S.R. ............................ 128/1 D

Primary Examiner—Edward M. Coven
Attorney, Agent, or Firm—Sughrue, Mion, Zinn, Macpeak and Seas

[57] ABSTRACT

A fluid isolator is used to separate a drive gas from a drive air. A pulsation in the air pressure is produced to drive a balloon pump placed within the aorta through the drive gas. The gas pressure on the secondary side is determined as the air pressure applied to the primary side of the isolator is a positive pressure, and the quantity of gas on the secondary side is automatically regulated in accordance with a result of such determination. The gas pressure may be controlled so as to coincide with a target value, or alternatively, the quantity of gas may be controlled in accordance with a difference between the gas pressure and the blood pressure of a physical body.

7 Claims, 17 Drawing Sheets

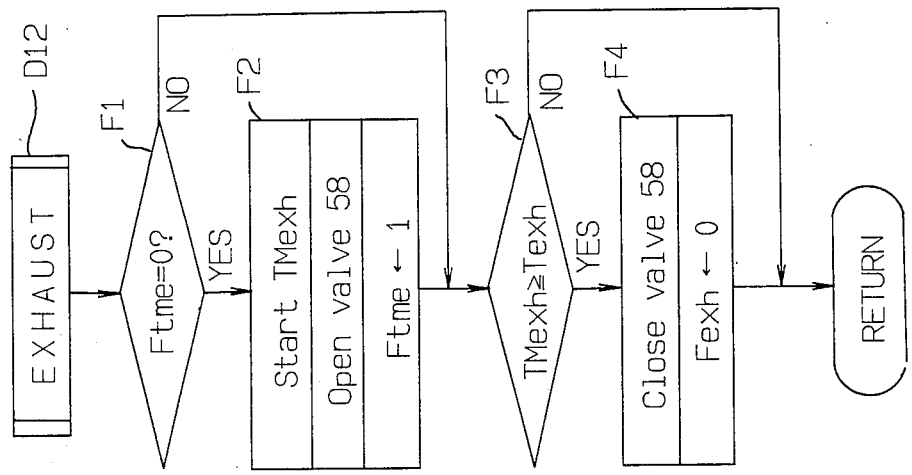
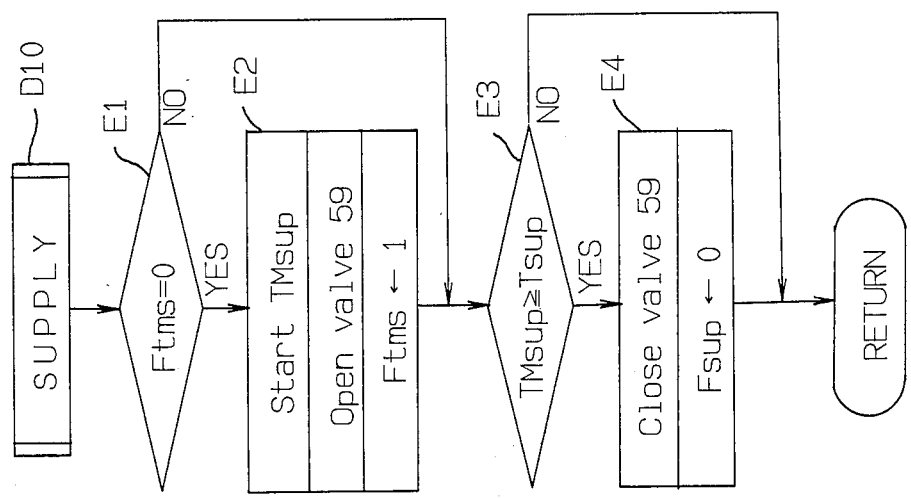

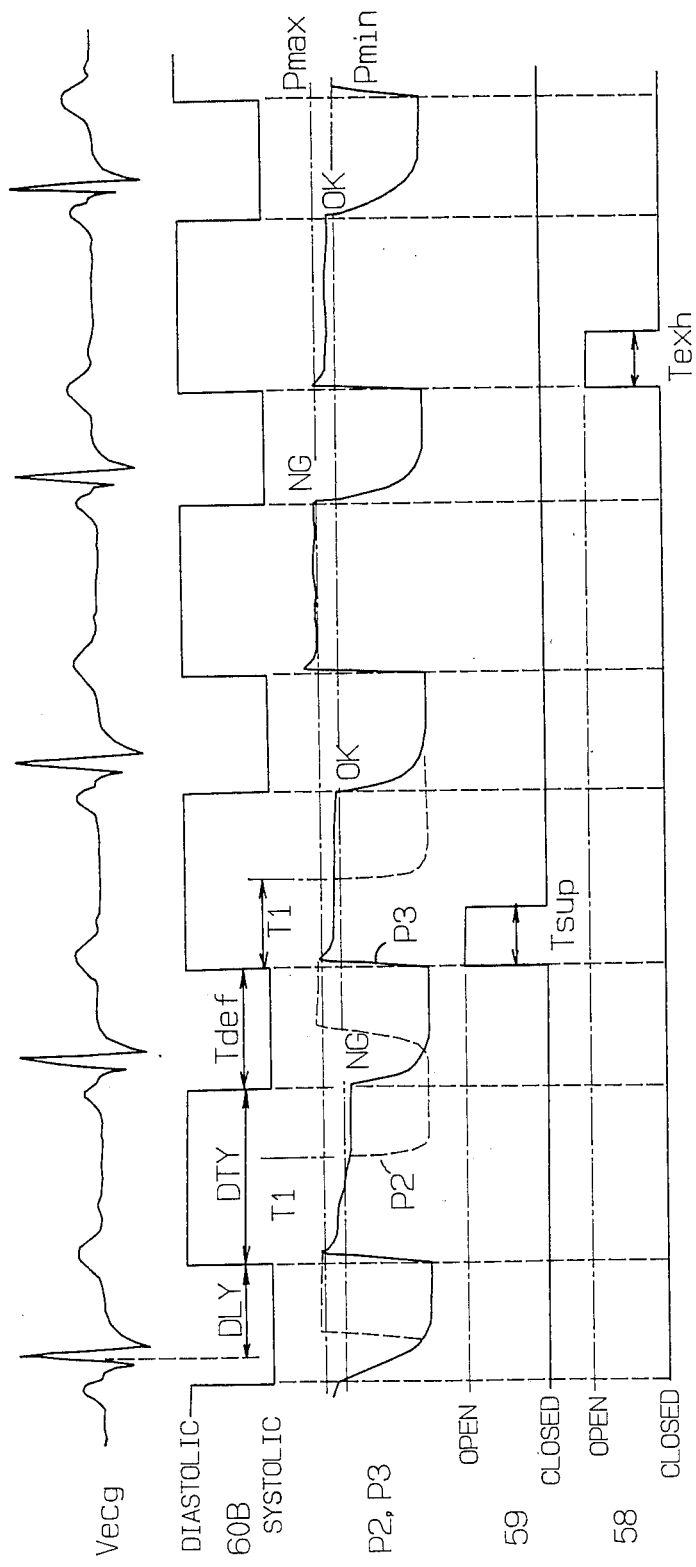

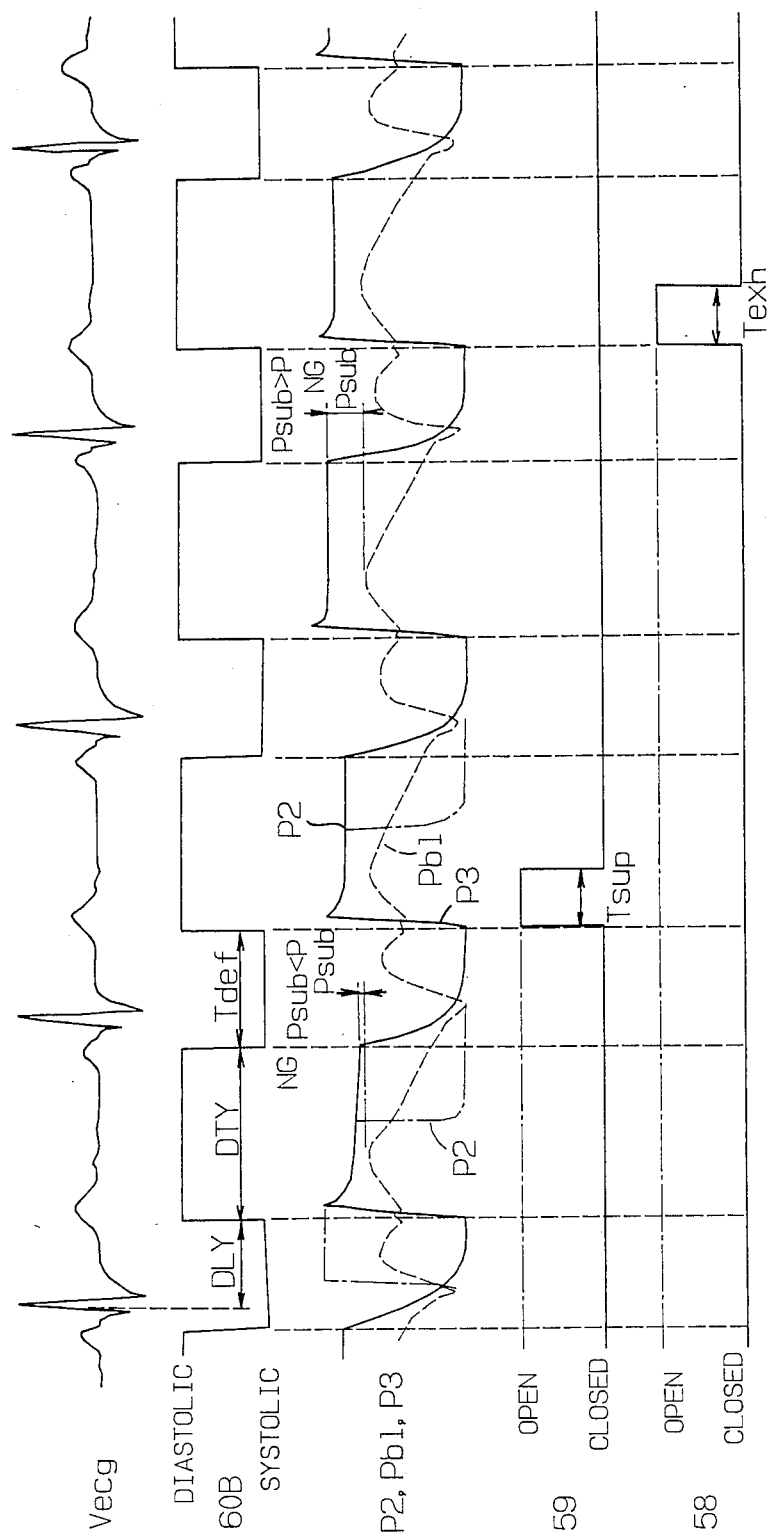

DRIVE UNIT FOR MEDICAL PUMP

BACKGROUND OF THE INVENTION

The invention relates to a drive unit which drives a medical pump used in a circulating system of a human body such as artificial heart or a balloon pump within the aorta, for example, in particular, to a drive unit for a medical pump which alternately delivers a positive and a negative pressure.

Considering a balloon pump disposed within the aorta, it is inflated in response to a positive pressure and deflated in response to a negative pressure applied thereto. Accordingly, a medical pump of the kind described performs a pumping operation in response to a repeated application of alternating positive and negative pressures. Such positive or negative pressure is applied to the pump from a given drive unit in terms of a fluid such as air or gas. An example of a drive unit for such medical pump is disclosed in U.S. Pat. No. 4,648,385.

It will be noted that to meet with the need of a varying size of the physical body of a user, an intra-aortal balloon pump is prepared in a variety of capacities. In a drive of the balloon pump, a required minimum amount of fluid, which depends on the capacity of the balloon pump being driven, should be supplied to the latter when it is to be expanded. It is preferred that the balloon be inflated and deflated at a high rate.

In an arrangement disclosed in U.S. Pat. No. 4,648,385, a fluid isolator is divided by a diaphragm into a primary and a secondary side, with an air pressure applied to the primary side while the secondary side is filled with helium gas to drive a balloon pump connected to the secondary side.

To accommodate for a change in the capacity of the balloon pump, the primary side of the fluid isolator is provided with a control member which controls the extent of movement of the diaphragm, so that the stroke of diaphragm is adjustable by adjusting the position of the control member. However, with this construction, when the balloon pump is changed, the stroke of a fresh balloon pump must be adjusted again depending on its capacity. Another factor which requires a consideration relates to the length of a hose which interconnects the balloon pump with its drive unit. When the length of the hose varies, the relationship between the capacity of the balloon pump and the stroke of the diaphragm also changes. Accordingly, the length of the hose cannot be changed at will. In addition, when the diaphragm abuts against the control member, the magnitude of a negative pressure applied to the balloon pump becomes saturated and is limited to a small value. Accordingly, when a smaller stroke is chosen, the resulting negative pressure will be reduced in magnitude, resulting in a retarded rate of deflation of the balloon pump.

SUMMARY OF THE INVENTION

It is an object of the invention to dispense with any adjustment when the capacity of a medical pump such as a balloon pump as well as the length of its associated hose are changed.

The above object is accomplished in accordance with the invention by providing pressure detecting means for detecting a pressure which is applied to a medical pump, and first and second valve means which regulate the quantity of fluid supplied to the secondary side of the fluid isolator. The pressure applied to the medical pump is determined when a positive pressure is applied to the primary side of the isolator, and the first and the second valve means are controlled in accordance with such determination.

When a positive pressure is applied to the primary side of the fluid isolator, the balloon pump expands. If the pressure in the primary side of the isolator exceeds the pressure of the secondary side, the diaphragm located within the isolator will come to a stop in abutment against a wall of the isolator on the secondary side. When the diaphragm comes to a stop, a further increase in the pressure of the secondary side is prevented. The resulting capacity of the secondary channel of the fluid isolator depends on the capacity of the balloon pump and the length of the drive hose. The balloon pump can be expanded properly by applying a given positive pressure to the balloon pump. Such positive pressure is substantially constant independently from the capacity of the balloon pump. Consequently, when the quantity of fluid in the secondary channel is controlled so that the secondary pressure coincides with a predetermined target value when a positive pressure is applied to the primary side of the isolator, the balloon pump is allowed to assume a properly expanded condition if the capacity of the balloon pump or the length of the drive hose changes. With this arrangement, there is no need to control the movement of the diaphragm on the primary side of the isolator. Within such control member, the secondary pressure will become equal to the primary pressure when a negative pressure is applied to the secondary side, thus allowing the balloon pump to be inflated more rapidly.

In one preferred embodiment of the invention to be described later, the secondary pressure (positive pressure) which prevails immediately before the primary pressure is changed from a positive to a negative pressure is compared against a given upper limit and lower limit to control the first and the second valve means, thus maintaining the secondary pressure in a range between the upper and the lower limit.

In another preferred embodiment, a pressure differential between the secondary pressure of the isolator when a positive pressure is applied to the primary side and the maximum value of the blood pressure is determined, and the first and the second valve means are controlled so as to maintain the pressure differential within a given range, thus regulating the quantity of fluid on the secondary side.

Other objects and features of the invention will become apparent from the following description of several embodiments thereof with reference to the drawings.

BRIEF DESCRIPTION OF THE DRAWINGS

FIGS. 7a, 7b, 7c, 7d, 7e, 7f, 7g, 7h and 7i are flowcharts illustrating the detail of the operation by the microcomputer 100 shown in FIG. 4;

FIGS. 8a and 8b are timing charts illustrating the operation of the unit shown in FIG. 1;

FIG. 9b is a series of timing charts illustrating the operation of the unit according to the embodiment shown in FIG. 9a.

DETAILED DESCRIPTION OF PREFERRED EMBODIMENTS

Figure 1:
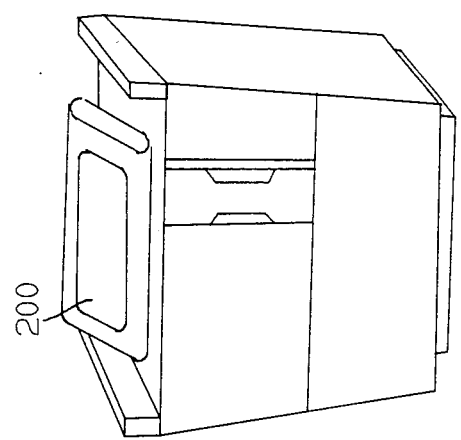
FIG. 1 is a perspective view, showing the appearance of a medical pump drive unit according to the invention.

FIG. 1 shows the appearance of a balloon pump drive unit according to the invention. The drive unit is adapted to be connected with a balloon pump 60B through a drive hose, not shown. On its top, the drive unit is provided with an operating board 200 which has an input function and a display function. The operating board 200 comprises a liquid crystal display unit and a key switch matrix comprising a pair of matrix-shaped, transparent electrode boards which are disposed in overlying relationship with the surface of the display unit, thus including a display section and an input section which are integrally constructed.

Figure 2:
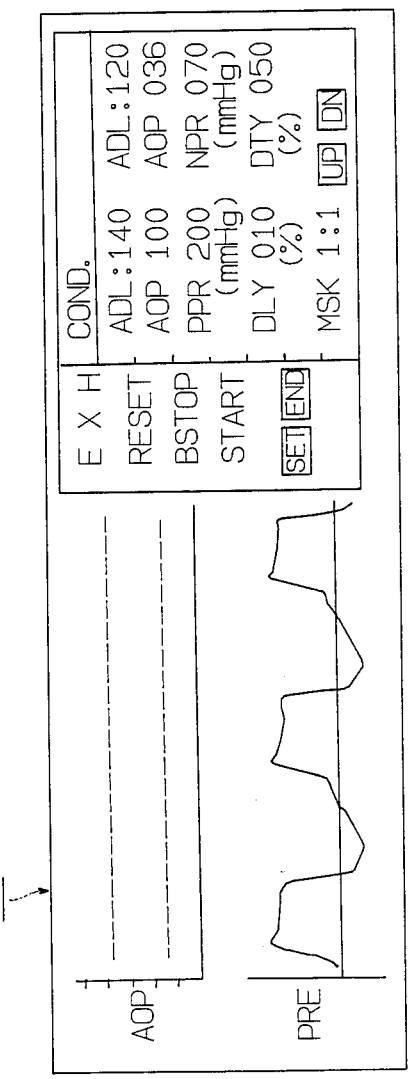
FIG. 2 is a plan view of an operating board of the unit shown in FIG. 1.

The appearance of the operating board 200 is shown in FIG. 2. Referring to FIG. 2, it will be noted that the left half of the board 200 includes a blood pressure display section which provides a graphical display of a change in the blood pressure (AOP) of a patient who has incorporated the balloon pump 60B with time, and a pressure display section which indicates the waveform of a fluid pressure (PRE) which is used to drive the balloon pump 60B.

It will be noted that a number of symbols and figures are indicated on the right half of the operating board. Specifically describing these symbols, "EXH" refers to a key switch which commands an exhaustion of gas from the balloon pump, "BSTOP" a key switch which commands stopping the drive of the balloon pump, "START" a key switch which commands starting the drive of the balloon pump, "SET" a key switch which commands the initiation of changing a drive parameter, and "END" a key switch which commands the termination of changing the drive parameter. All of these symbols are visible within the liquid crystal display unit.

Continuing the description of symbols and figures appearing on the right half of the operating board, "AOP 100" and "AOP 036" indicates a maximum or systolic blood pressure of 100 mmHg and a minimum or diastolic blood pressure of 36 mmHg. "PPR 200" and "NPR 070" indicate that the drive unit uses a positive pressure of 200 mmHg and a negative pressure of 70 mmHg. "DLY 010" indicates that the time interval (DLY) from the appearance of R-wave on the cardiogram to the expansion of the balloon pump has 10% duty cycle with respect to the pulse period. "DTY 050" indicates that the time interval during which the balloon pump expands (DTY) has a 50% duty cycle with respect to the pulse period. "MSK 1:1" indicates that the ratio (MSK) of the number of pulse signals to the number of times the balloon pump is triggered to be driven has a one-to-one correspondence. When a mask operation is involved, the ratio changes. "UP" and "DN" refer to key switches which command updating a parameter up and down, respectively. By way of example, when the key switch "SET" is depressed followed by the depression of the key switch "DLY" and then followed by the depression of the key switch "UP", the parameter DLY will be incremented. When the key switch "END" is depressed, the updated result is registered as a new parameter.

Figure 3:
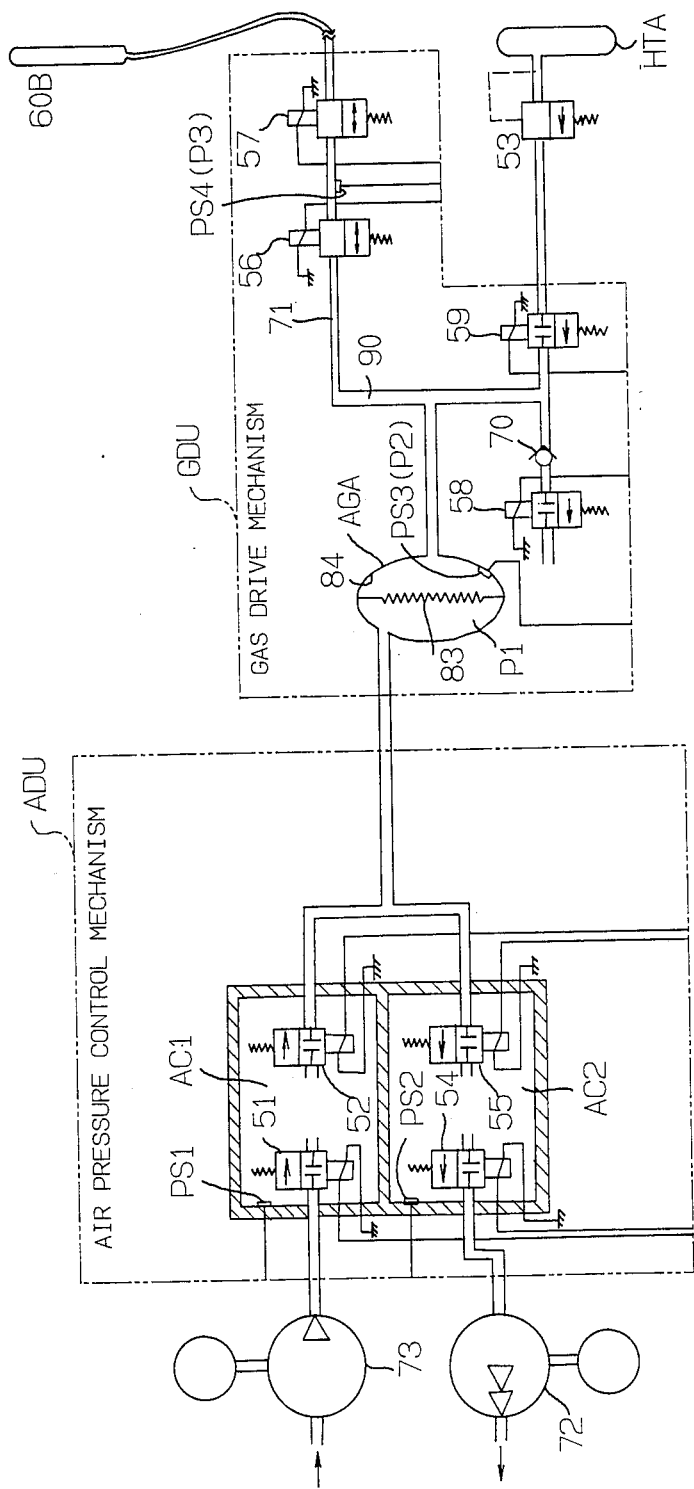
FIG. 3 is a block diagram of an internal mechanism of the unit shown in FIG. 1.

FIG. 3 shows the internal construction of the drive unit shown in FIG. 1. The unit includes a compressor 73 which functions as a source of positive pressure and a vacuum pump which functions as a source of negative pressure. An air pressure control mechanism ADU includes a positive pressure system and a negative pressure system. Specifically, the positive pressure system comprises an accumulator AC1, and a pair of solenoid valves 51 and 52, which are disposed within the accumulator AC1. The valve 51 has its inlet connected to the output of the compressor 53 and its outlet left opening into the accumulator AC1. The valve 52 has its inlet opening into the accumulator AC1 and its outlet taken out of the accumulator. The negative pressure system comprises an accumulator AC2 and a pair of solenoid valves 54 and 55, which are disposed within the accumulator AC2. The valve 54 has its inlet connected to the output of the vacuum pump 52 and its outlet opening into the accumulator AC2. The valve 55 has its inlet opening into the accumulator AC2 and its outlet taken out of the accumulator. A pressure sensor PS1 is disposed within the accumulator AC1, and similarly a pressure sensor PS2 is disposed within the accumulator AC2 for detecting the pressure of the respective systems. It will be noted that the outlet of the valve 52 and the outlet of the valve 55 are connected together and connected to the inlet of a gas drive mechanism GDU.

The gas drive mechanism GDU comprises a fluid isolator AGA, solenoid valves 56, 57, 58 and 59, a check valve 70 and pressure sensors PS3, PS4. The fluid isolator AGA comprises a hollow housing in which a displaceable diaphragm 83 is disposed to divide the internal space into a primary and a secondary side. The detail of the construction may be similar to the disclosure of U.S. Pat. No. 4,648,385 except that in the present instance, there is no mechanism which controls the stroke of the diaphragm 83 on the primary side. The primary channel of the isolator is connected to the output of the air pressure control mechanism ADU or the outlets of the valves 52, 55. The pressure sensor PS3 is disposed within the secondary space of the isolator AGA. The isolator AGA has a secondary channel 71 which is connected through the valves 56 and 57 to the balloon pump 60B. The valve 59 has its one end connected to the channel 51 and the other end connected to a helium gas cylinder HTA through a reducing valve 53. The valve 58 has its one end connected to the channel 71 through the check valve 70 and its other end left open to the atmosphere. The pressure sensor PS4 is disposed in a channel between the valves 56 and 57.

Figure 4:
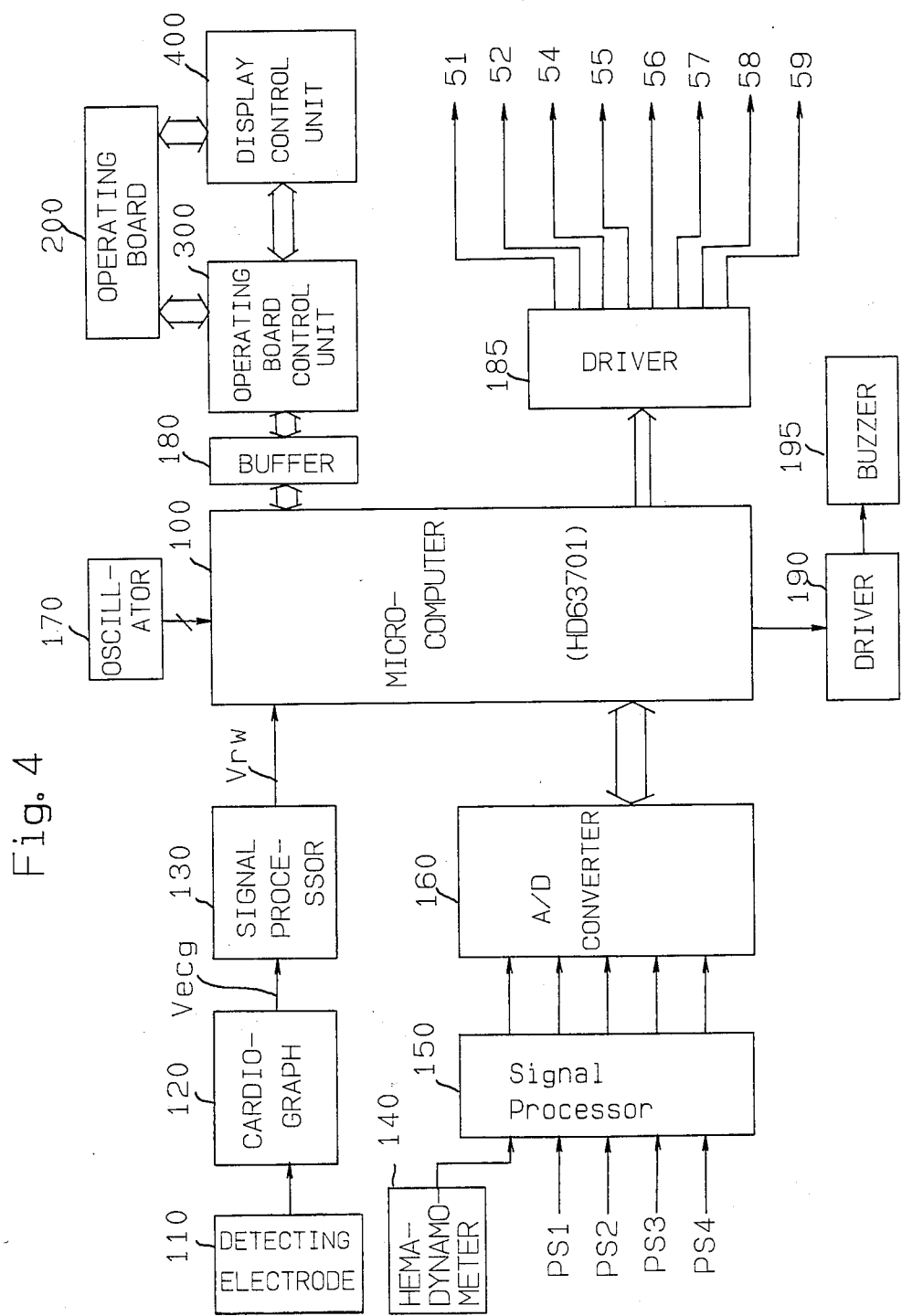
FIG. 4 is a block diagram of an electrical circuit used in the unit shown in FIG. 1.

FIG. 4 shows a block diagram of an electrical circuit which is contained in the drive unit shown in FIG. 1. Referring to FIG. 4, the electrical circuit includes a microcomputer 100, a detecting electrode 110, a cardiograph 120, a signal processor circuit 130, a hemadynamometer 140, another signal processor circuit 150, A/D (analog/digital) converter 160, an oscillator 170, a buffer 180, drivers 185, 190, a buzzer 195, the operating board 200, an operating board control unit 300 and a display control unit 400.

A microcomputer HD63701 manufactured by Hitachi Manufacturing Co., is used for the microcomputer 100. The detecting electrode 110 is attached to the physical body of a patient in order to detect an electrical signal which corresponds to a heart movement. The cardiograph 120 is similar to the one which is usually employed to obtain a cardiogram. It amplifies the electrical signal from the electrode 110 and removes noises therefrom to deliver a signal Vecg (see FIG. 8a). The signal processor circuit 130 extracts R-wave (Wr) component from the signal Vecg by the frequency discrimination, and then digitizes it at a predetermined threshold level to deliver a binary signal Vrw. Thus, the signal Vrw represents a pulse signal which appears with a timing of R-wave on the cardiogram. The signal Vrw is applied to an interrupt request terminal of the microcomputer 100.

Hemadynamometer 140 is a transducer which delivers an electrical signal depending on the blood pressure of a patient. It will be noted that outputs from the hemadynamometer 140 and the pressure sensors PS1, PS2, PS3 and PS4 are fed to the signal processor circuit 150, which then operate to amplify the input signal or signals and to remove noises therefrom. The circuit 150 has corresponding output terminals which are connected to individual analog input terminals of the converter 160. The converter 160 is connected to input and output ports of the microcomputer 100 so as to perform an A/D conversion of an electrical signal applied to a selected one of its analog input terminals and to deliver the resulting digital data to the microcomputer 100 in response to an instruction from the microcomputer 100.

The driver 185 is connected to output ports of the microcomputer 100 and has several output terminals which are individually connected to the drive solenoids of the valves 51, 52, 54, 55, 56, 57, 58 and 59. The driver 190 is similarly connected to output ports of the microcomputer 100 and has an output terminal which is connected to the control terminal of the buzzer 195. The operating board control unit 100 is connected to a serial communication bus of the microcomputer 100 through the bus buffer 180.

Figure 5A:
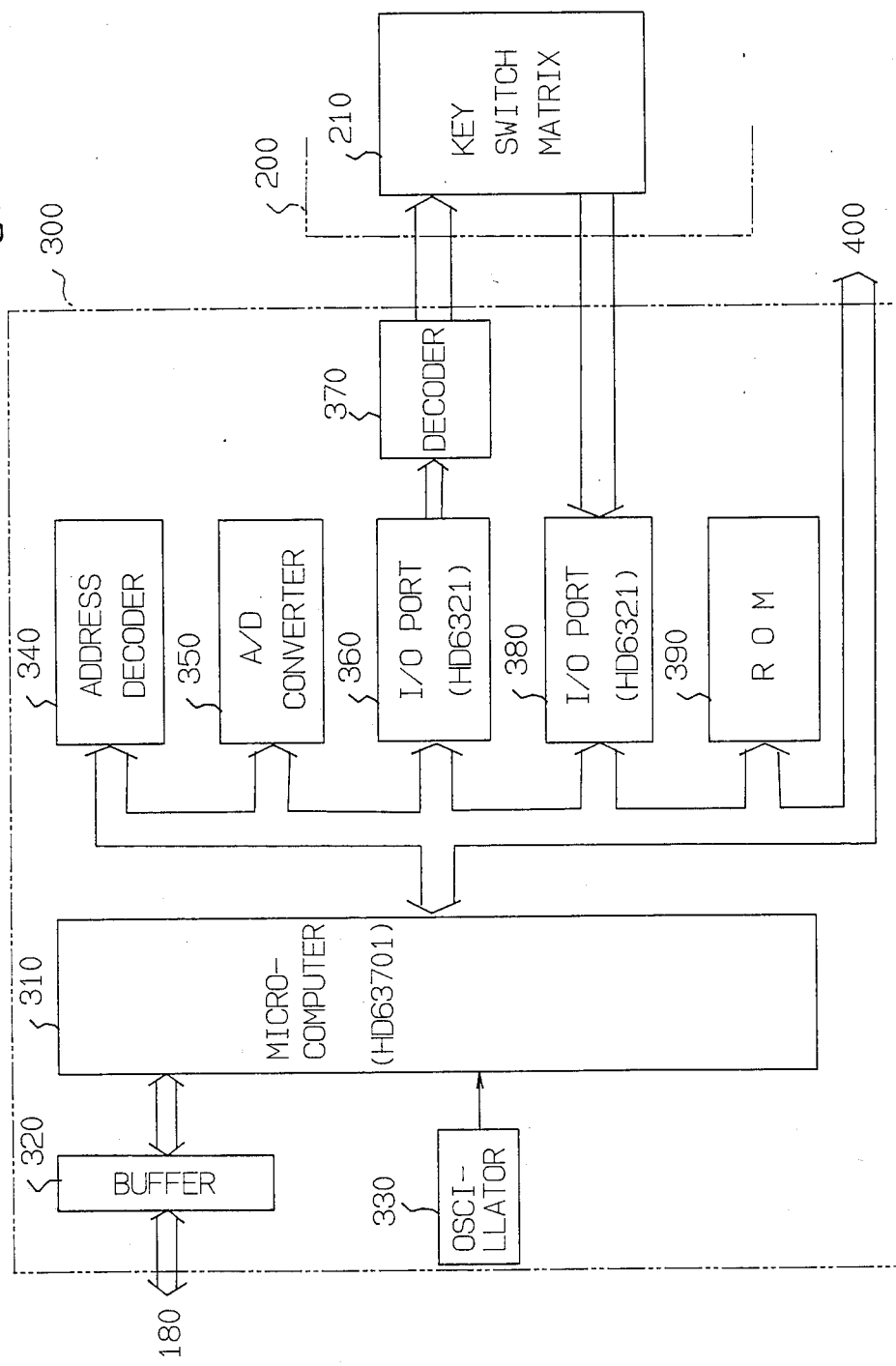
FIGS. 5a and 5b are block diagrams of operating board control unit 300 and display control unit 400 both shown in FIG. 4.

The arrangement of the operating board control unit 100 is illustrated in FIG. 5a. This unit includes a microcomputer 310, a buffer 320, an oscillator 330, an address decoder 340, A/D converter 350, I/O port unit 360, another decoder 370, another I/O port unit 380 and read only memory (ROM) 390. A microcomputer HD63701 manufactured by Hitachi Manufacturing Co., is used for the microcomputer 310. The serial communication bus of the microcomputer 310 is connected to the bus buffer 180 through the bus buffer 320. The display control unit 400 is also connected to the microcomputer 310.

The address decoder 340 decodes address information which is output from the microcomputer 310 to form a plurality of chip select signals which select various devices such as the converter 350, I/O port units 360 and 380, ROM 390 and the display control unit 400.

I/O port unit 360 operates as an output port unit, and a signal which is output therefrom is decoded by the decoder 370 to be applied as a scan signal to a key switch matrix 210 on the operating board. I/O port unit 380 operates as an input port unit, receiving electrical signals representing the status of various key switches within the key switch matrix 210 for purpose of entry. Accordingly, the microcomputer 310 is capable of reading the status of the various keys by controlling the scanning of the key switch matrix 210 through the I/O port units 360 and 380. ROM 390 stores operating program data associated with the microcomputer 310 and display data.

Figure 5B:
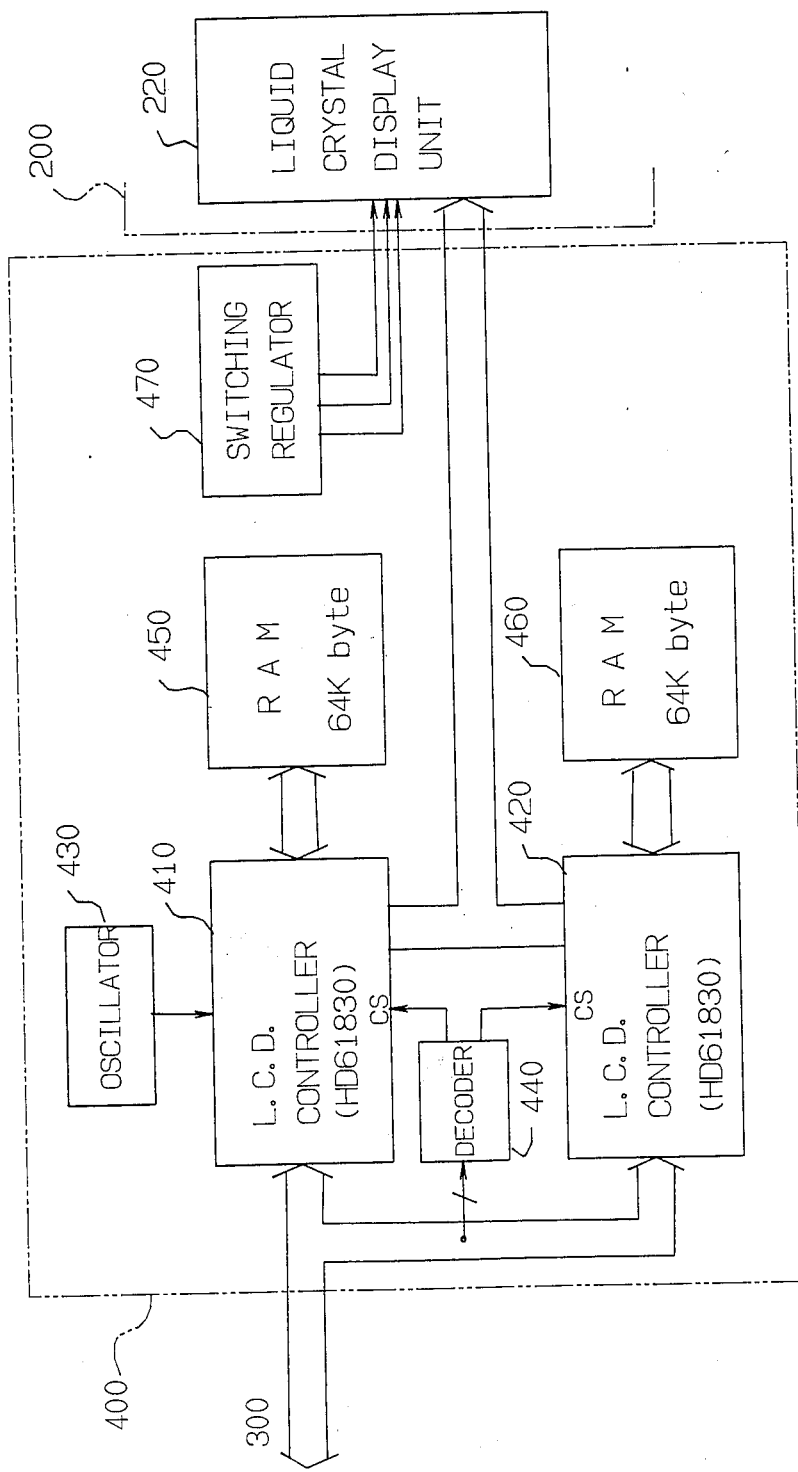

The arrangement of the display control unit 400 is illustrated in FIG. 5b. As shown, the unit includes LCD (liquid crystal display) controllers 410, 420, an oscillator 430, a decoder 440, RAM's (read-write memories) 450, 460 and a switching regulator 470. Controllers HD61830 manufactured by Hitachi Manufacturing Co., are used for the LCD controllers 410 and 420.

LCD controllers 410 and 420 are connected to the operating board control unit 300. The controllers 410 and 420 operate to display visual information which corresponds to data stored in RAM's 450 and 460, respectively, on the liquid crystal display unit 220 of the operating board. The switching regulator 470 produces and supplies the power required by the display unit 220.

Figure 6:
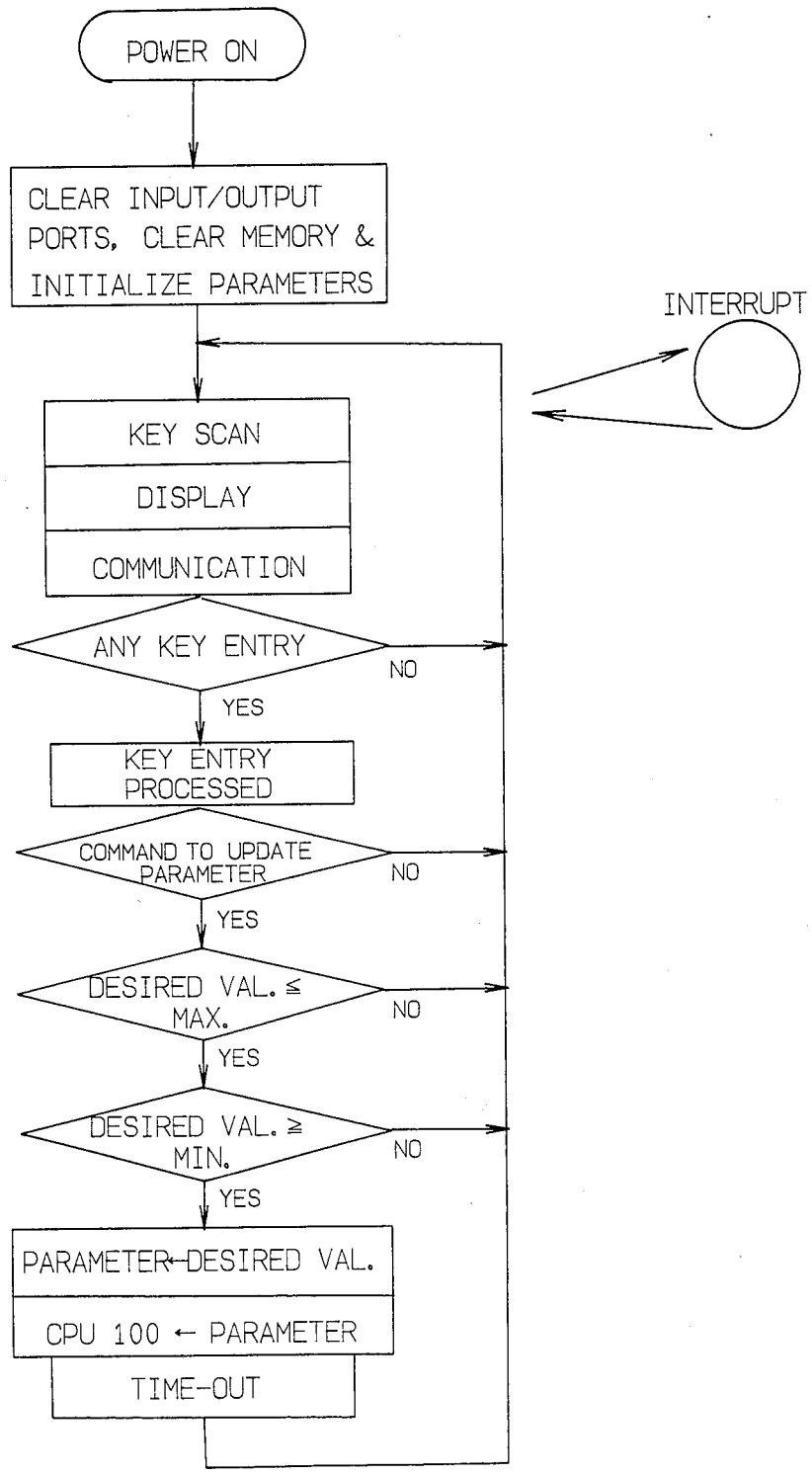
FIG. 6 is a flowchart generally illustrating a control operation by a microcomputer 310.

FIG. 6 is a flowchart illustrating the operation of the microcomputer 310 within the operating board control unit 300. When the power is turned on, the input and output ports of the microcomputer 310 are cleared to their initialized conditions, the memory content is cleared, and various parameters are preset to predetermined initial values.

A key scan, display and a communication processing then follow. During the key scan, the scan over the key switch matrix 210 is controlled while reading the status of various keys. During the display processing, data which corresponds to any fresh information to be displayed is loaded into the display control unit 400 in the event a key switch is operated, a parameter has been updated or in the event of occurrence of an abnormality. During the communication processing, if a change in the operation mode or an updating of a parameter has been commanded by the operation of a key switch, new information which corresponds to such command is transmitted to the microcomputer 100. When a key entry exists, a processing operation which corresponds to each key is executed. When there is a command to update a parameter, a desired value to which the parameter should be updated is compared against an upper limit and a lower limit which are prdetermined for the parameter, and the parameter is updated only when the desired value is in a range defined by the both limits. Whenever the parameter is updated, fresh parameter is transmitted to the microcomputer 100. If data is oncoming from the microcomputer, such data is received by an interrupt operation and is stored in a given memory.

Figure 7A:
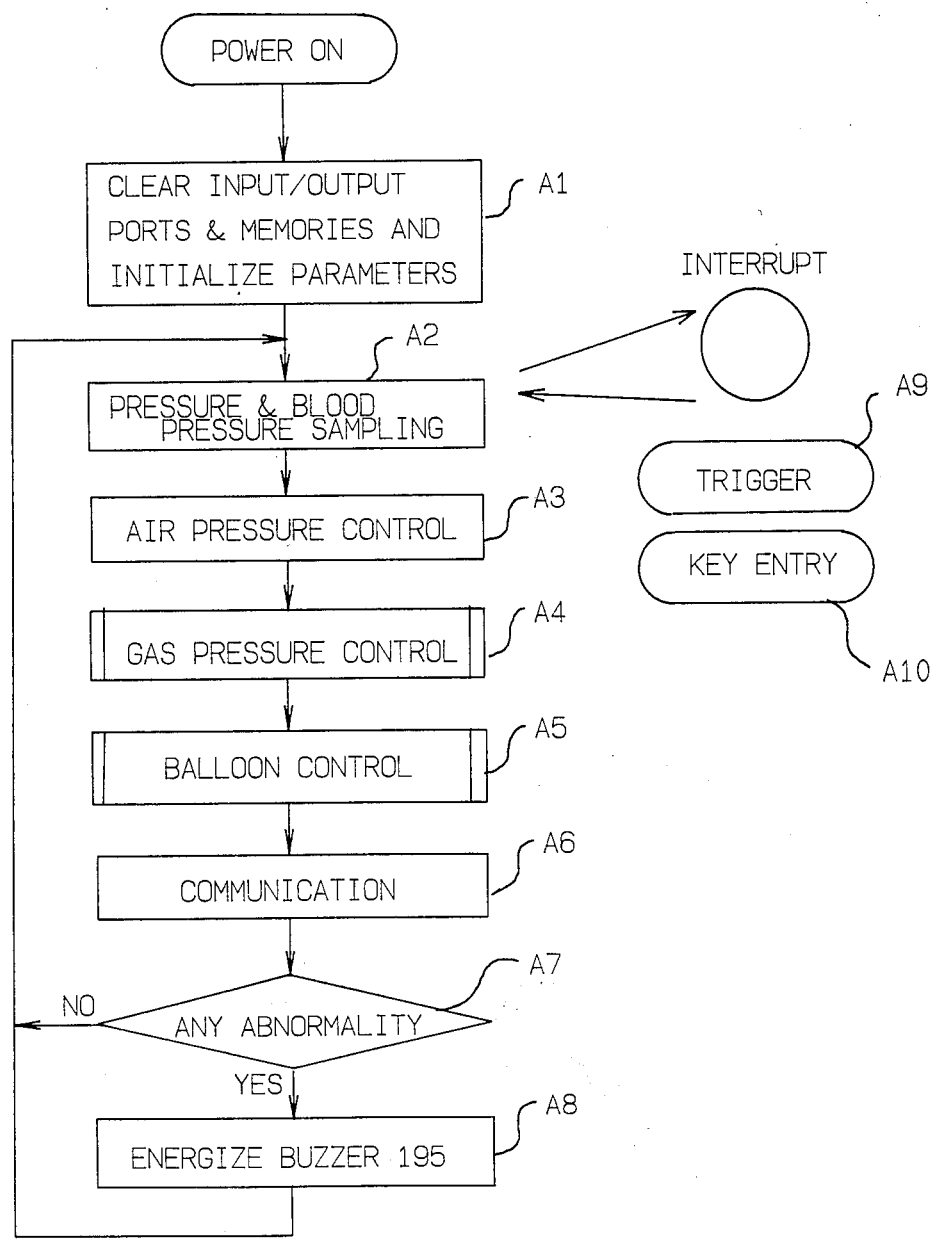

FIG. 7a is a flowchart which illustrates the operation of the microcomputer 100 schematically. When the power is turned on, input and output ports are cleared to their initial conditions, and the content of memories is also cleared, thus resetting operating parameters to predetermined initial values. Then follow a pressure/blood pressure sampling step, an air pressure control subroutine, a gas pressure control subroutine, a balloon control subroutine and a communication step, which are executed in a sequential manner. Such loop is repeated over and over again. In the event any abnormality has occurred, the buzzer 195 is energized. An interrupt request by the signal Vrw is responded to by performing a "trigger" operation by an interrupt operation. In response to a communication interrupt request from the operating board control unit 100, a "key entry" operation is performed by an interrupt operation.

Figure 7C:
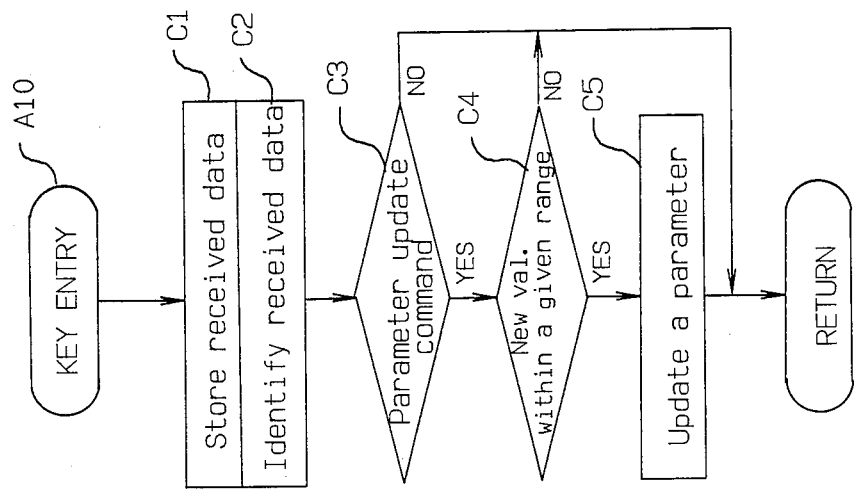
Figure 7B:
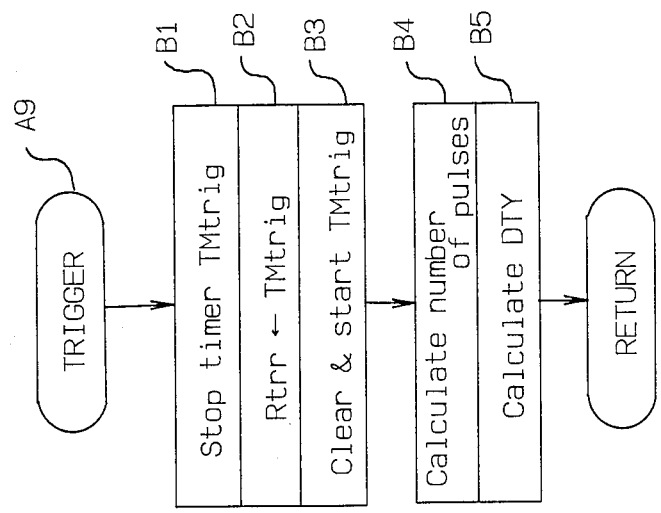
Figure 8A:
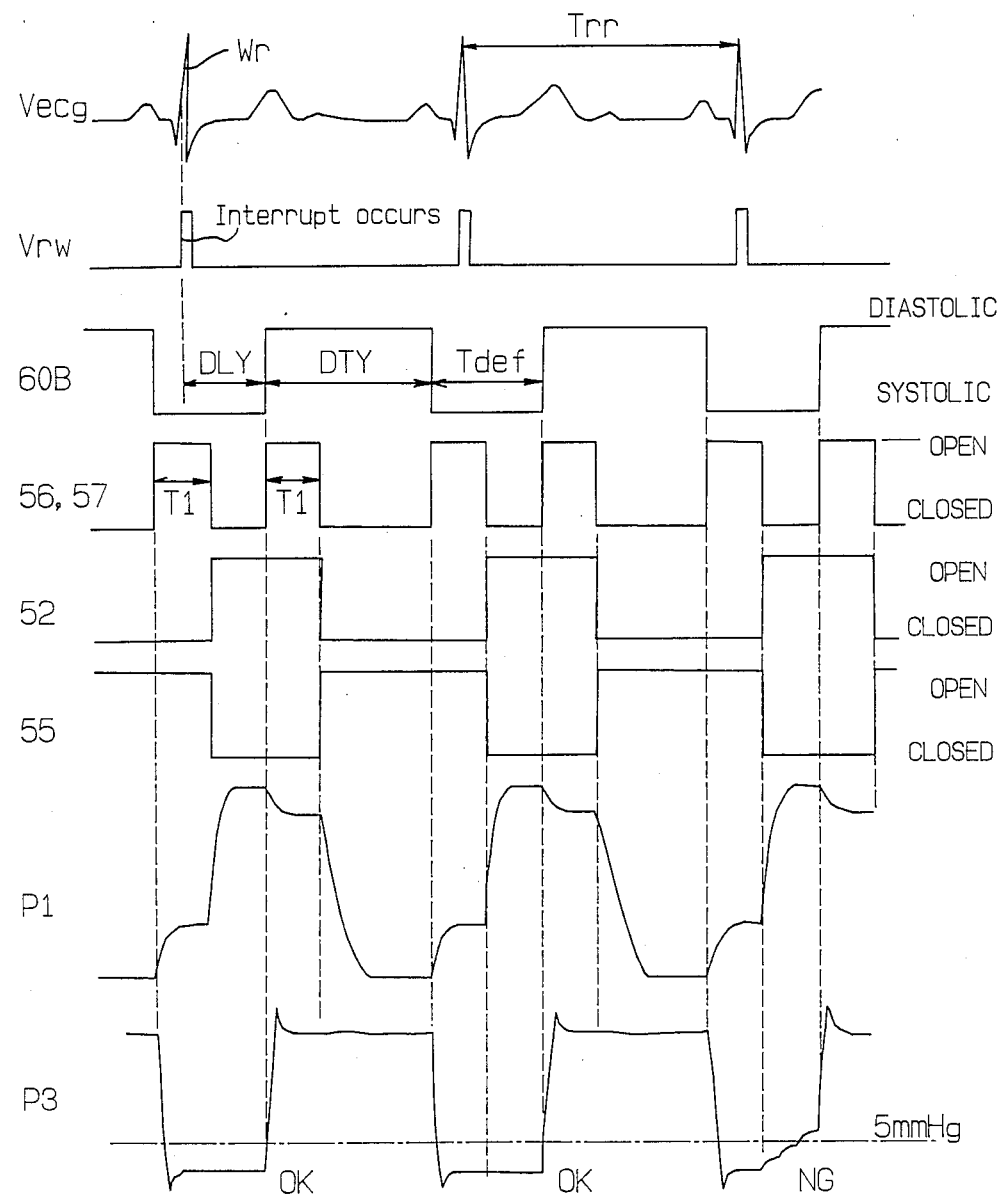

The detail of the trigger interrupt routine A9 is shown in FIG. 7b. In this routine, a trigger timer TMtrig is stopped, and the count therein is stored in a register Rtrr, whereupon the timer TMtrig is cleared and re-started. In this manner, the timer TMtrig operates to count the time interval from one interrupt to the next interrupt, which is represented by the signal Vrw. As illustrated in FIG. 8a, each time R-wave Rw appears on the cardiogram, a pulse appears for the signal Vrw, and the rising edge of the pulse produces an interrupt request. In this manner, the timer TMtrig counts the period Trr with which the R-wave occurs or the pulse period.

The number of pulses, the balloon expansion interval DTY and delay time DLY are calculated utilizing the period Trr which is determined by the timer TMtrig. It will be noted that when utilizing the operating board 200, the values of DTY and DLY are established in terms of a duty cycle (percent) with respect to the pulse period Trr, and hence the time intervals DTY and DLY change with a change in the pulse period. For this reason, the time intervals DTY and DLY are calculated each time the pulse period Trr is determined.

FIG. 7c is a flowchart illustrating the key entry interrupt routine A10. In this routine, data delivered from the microcomputer 310 is received and stored in a given memory, and then an identification of such data is made in order to perform a corresponding processing operation. If such data represents a parameter update command a desired value to which the parameter is to be changed is compared against the upper and the lower limit value of the parameter to see if the desired value is within a range defined by these limit values. If the desired value lies within the range, the updating of the parameter is enabled.

Returning to FIG. 7a, during the pressure/blood pressure sampling routine, electrical signals which are output from the hemadynamometer 140, and the pressure sensors PS1, PS2, PS3 and PS4 are sequentially sampled and subject to A/D conversion, thus obtaining digital data corresponding to the blood pressure and the individual pressures.

In the air pressure control routine A3, data representing the pressures which prevail within the accumulators AC1 and AC2, obtained as a result of the pressure/blood pressure sampling routine, are compared against respective predetermined target pressures for controlling the opening or closing of the solenoid valves 51 and 54 accordingly. Specifically, if the pressure detected by the sensor S1 is greater than the target pressure, the solenoid valve 51 is closed while it is opened when the detected pressure is less than the target pressure. The detail of such control is disclosed in U.S. Pat. No. 4,648,385. It is to be understood that the pressure in one of the accumulators, for example, AC1, is maintained at a predetermined target value of positive pressure while the pressure within the other accumulator AC2 is maintained at a target value of negative pressure.

Figure 7D:
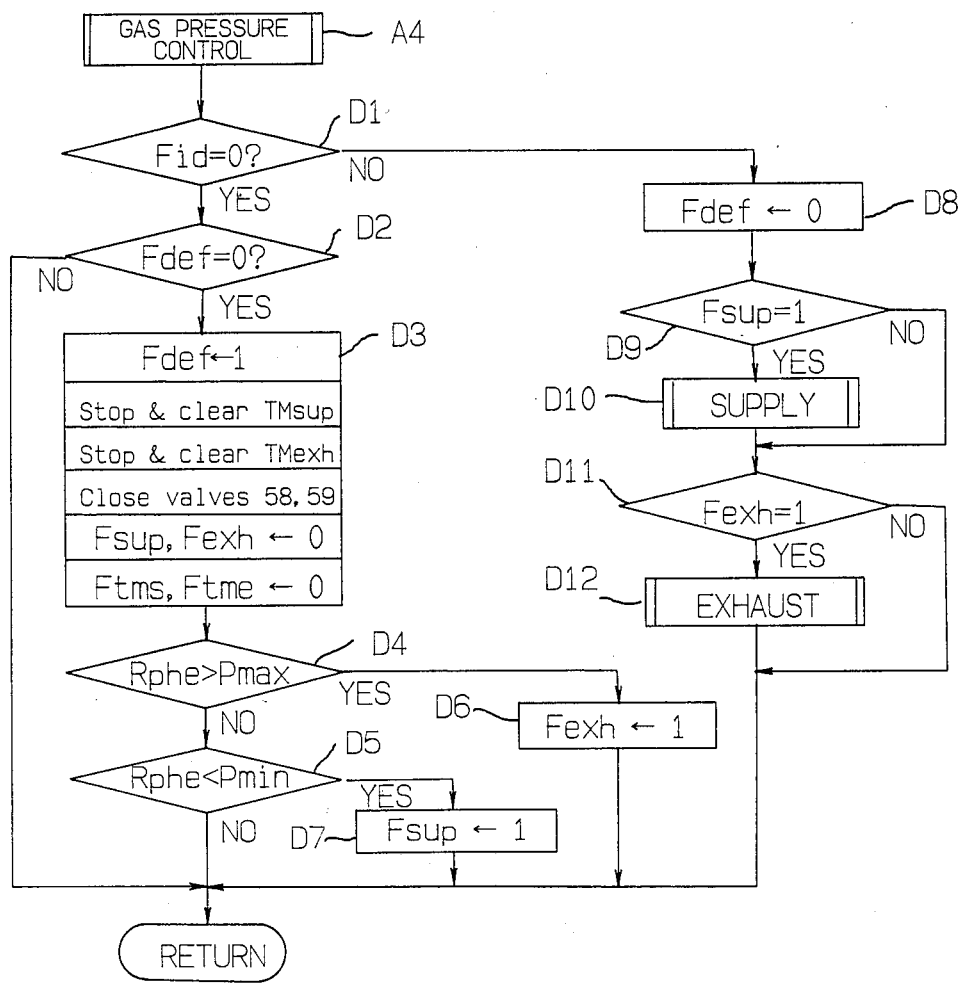

FIG. 7d is a flowchart illustrating the detail of the gas pressure control routine A4. In this routine, a flag Fid is examined. This flag is set to "1" when the balloon pump 1 is being inflated, and is reset to "0" when it is deflated. When the flag Fid is "0", indicating that the balloon pump is in its systole, another flag Fdef is then examined, and if it is "0", the next following processing operation is executed. Initially, the flag Fdef is set to "1", a timer TMsup which counts the time interval during which the gas is supplied is stopped and cleared. Another timer TMexh which counts the time interval during which the gas is exhausted is stopped and cleared, the solenoid valves 51 and 59 are set for closing movement, and flags Fsup, Fexh, Ftms and Ftme are cleared to "0".

The content of a register Fphe is then compared against a predetermined upper limit pressure value Pmax. If Rphe>Pmax, an exhaust flag Fexh is set to "1". If the reverse is true, the content of the register Rphe is compared against a predetermined lower limit pressure value Pmin. If Rphe<Pmin, a gas supply flag Fsup is set to "1". It will be understood that when the content of the register Rphe is intermediate Pmax and Pmin, the both flags Fexh and Fsup assume "0". As will be described later, the content of the register Rphe which then prevails represents the pressure detected by the sensor PS3 immediately before the air pressure applied to the primary side of the fluid isolator AGA is switched from a positive to a negative pressure. Accordingly, the flags Fsup and Fexh are set or reset depending on whether the secondary pressure of the isolator AGA when a positive pressure is applied thereto remains within a given range.

Upon execution of this routine, the flag Fdef is set to "1", and hence the described operation is not executed unless this flag is cleared to "0" as a result of other processing operations. In this manner, this routine is executed only once each time the balloon pump is in its systole. When the flag Fid is "1", indicating that the balloon pump is in its diastole, the program proceeds to a step D8. The flag Fdef is cleared to "0", and the air supply flag Fsup is examined. If the flag Fsup is "1", the air supply subroutine SUPPLY is executed. Subsequently the exhaust flag Fexh is examined and if this flag is equal to "0", the exhaust subroutine EXHAUST is executed.

The detail of the air supply subroutine SUPPLY and the exhaust subroutine EXHAUST are illustrated in FIGS. 7e and 7f, respectively. Referring to FIG. 7e, the subroutine SUPPLY will be described first. In this subroutine, a flag Ftms is initially examined. This flag assumes "0" initially. When the flag Ftms is "0", an air supply timer TMsup is started, the solenoid valve 59 is set to be open, and the flag Ftms is set to "1". The content of the timer TMsup is compared against a predetermined time interval Tsup. If TMsup≧Tsup, the solenoid valve 59 is set to be closed and the flag Fsup is cleared to "0". Thus, in the subroutine SUPPLY, the solenoid valve 59 is opened simultaneously with starting the timer TMsup, and this valve is closed after a given time interval (Tsup) has passed. During the time the valve 59 is open, helium gas is supplied to the channel 71 from the helium gas cylinder HTA through the reducing valve 53. Accordingly, the execution of the subroutine SUPPLY increases the quantity of the gas within the channel 71.

Referring then to FIG. 7f, the subroutine EXHAUST will be described. In this subroutine, a flag Ftme is initially examined. This flag is initially equal to "0". If the flag Ftme is "0", an exhaust timer TMexh is started, the solenoid valve 58 is set to be open and the flag Ftme is set to "1". The content of the timer TMexh is then compared against the predetermined time interval Texh. If TMexh≧Texh, the valve 58 is set to be closed and the flag Fexh is cleared to "0". Thus, in the subroutine EXHAUST, the solenoid valve 58 is opened simultaneously with starting the timer TMexh, and the valve is then closed after a given time interval Texh. During the time the valve 68 is open, the helium gas within the channel 71 is discharged into the atmosphere. Accordingly, the execution of the subroutine EXHAUST reduces the quantity of gas within the channel 71.

In the present embodiment, the magnitude of a positive pressure applied to the primary side of the fluid isolator AGA is sufficiently greater than the secondary pressure when the balloon pump is inflating. Accordingly, when the balloon pump is inflating, the diaphragm 83 of the fluid isolator remains at rest in abutment against the wall 84 of the secondary side of the isolator. In this instance, the volume of the secondary channel 71 of the isolator is determined by the volume of the balloon pump 60B itself when expanded and the volume of a flow path which connects the balloon pump with the secondary side of the isolator. Since the latter remains constant in volume, the volume of the channel 71 depends on the capacity of the balloon pump 60B. While a variety of capacities are available for the balloon pump, it is to be noted that the pressure which is required to achieve a full inflation remains substantially constant. Accordingly, in the present embodiment, the quantity of helium gas within the channel 71 is automatically regulated so that the secondary pressure of the isolator remains in a range between Pmax and Pmin when the diaphragm remains at rest as a positive pressure is applied to the primary side of the fluid isolator AGA. Accordingly, if the capacity of a particular balloon pump used changes, no special adjustment is required. In the present example, the primary side of the fluid isolator AGA is provided with sufficiently extensive space so that the extent of movement of the diaphragm 84 is not interfered with as by abutment against the wall when a negative pressure is applied thereto. If the movement of the diaphragm is interfered with, the negative pressure which is applied to the secondary side will be reduced. In this manner, the secondary pressure of the isolator when a negative pressure is applied to the isolator AGA is maintained substantially equal to the primary pressure and is high enough (in absolute value) to permit the deflation of the balloon pump 60B to be completed within a reduced length of time when a negative pressure is applied. The attention of the reader is directed to FIG. 8b which illustrates one example of the timing relating to the gas pressure control.

Figure 7G:
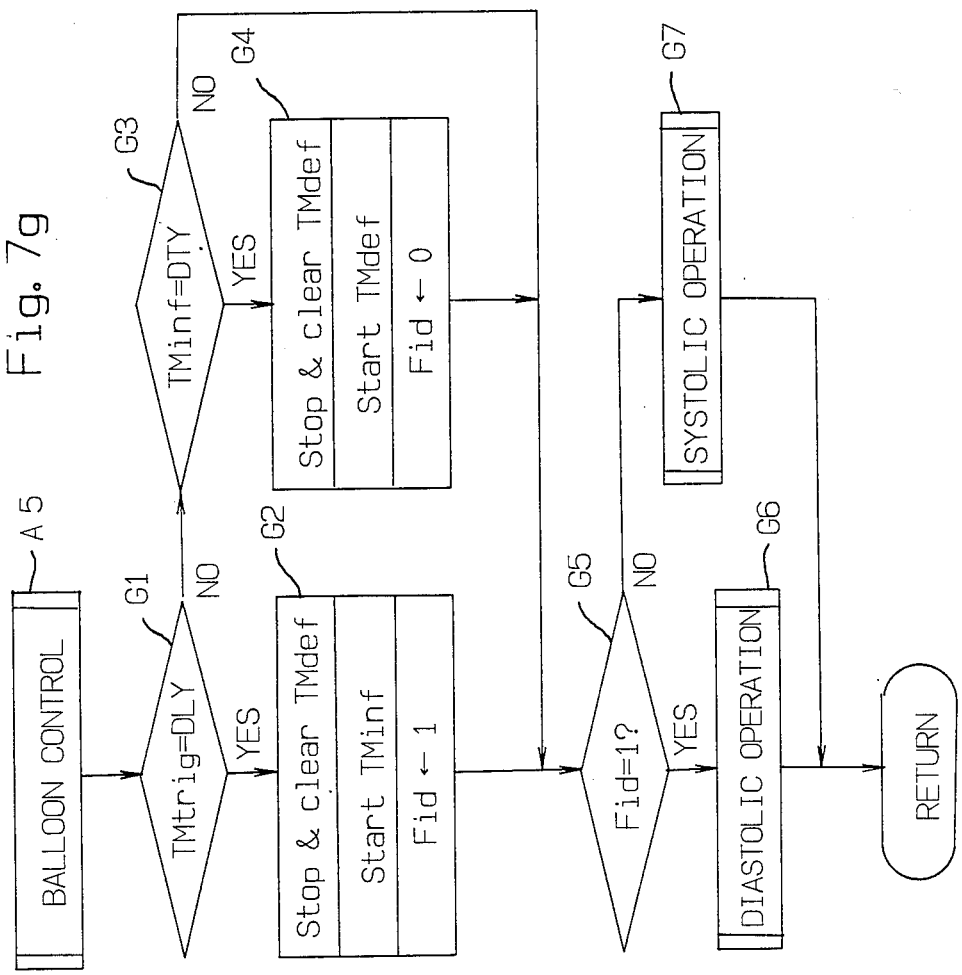

The detail of the balloon control subroutine A5 shown in FIG. 7a is illustrated in FIG. 7g. In this subroutine, the content of the trigger timer TMtrig is compared against the delay time DLY. When the time which has passed since the occurrence of an interrupt (trigger) by the signal Vrw coincides with the delay time DLY, the program proceeds to a step G2 where a deflation timer TMdef is stopped and cleared, an inflation timer TMinf is started, and the flag Fid is set to "1". When the equality between TMtrig and DLY is not reached, the content of the inflation timer TMinf is compared against the expansion interval DTY. If TMinf=DTY, the program proceeds to a step G4, where the inflation timer TMinf is stopped and cleared, the deflation timer TDdef is started and the flag Fid is cleared to "0". Thus, the timer TMtrig continues its counting operation until the given interval DLY passes since the interrupt request by the signal Vrw has occurred while the timer TMinf continues its counting operation over a given time interval DTY since the equality between TMtrig and DLY is established or during the time the balloon pump is inflating, and the timer TMdef begins its counting operation when the timer TMinf has stopped its operation and continues its counting operation until the content of the timer TMtrig is equal to DLY or during the time the balloon pump is deflating. The flag Fid assumes "1" when the balloon pump 60B is inflating and assumes "0" when it is deflating. The diastolic subroutine is executed when the flag Fid is "1" and the systolic subroutine is executed when the flag Fid is "0", independently from the values in the timers TMtrig and TMinf.

Figure 7H:
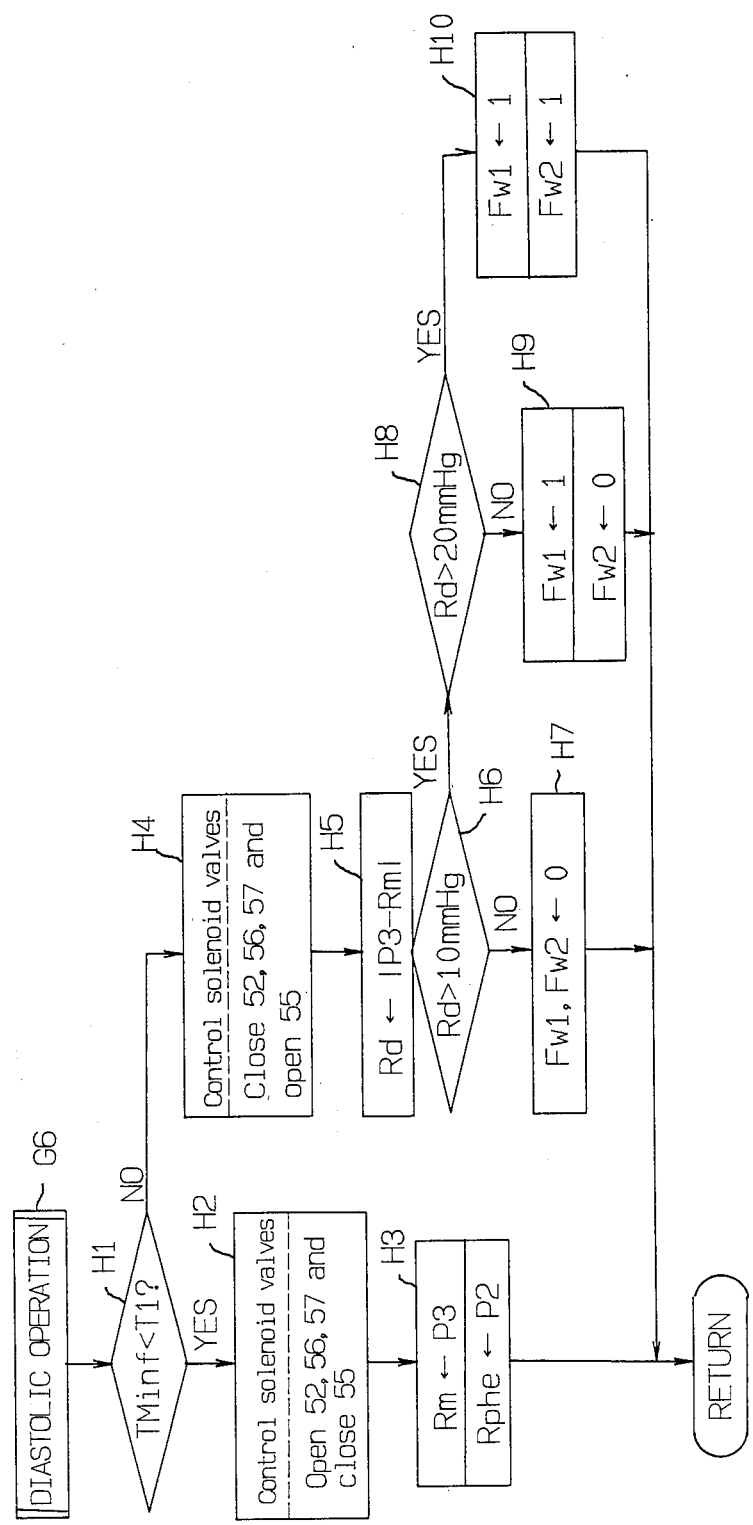
Figure 7I:
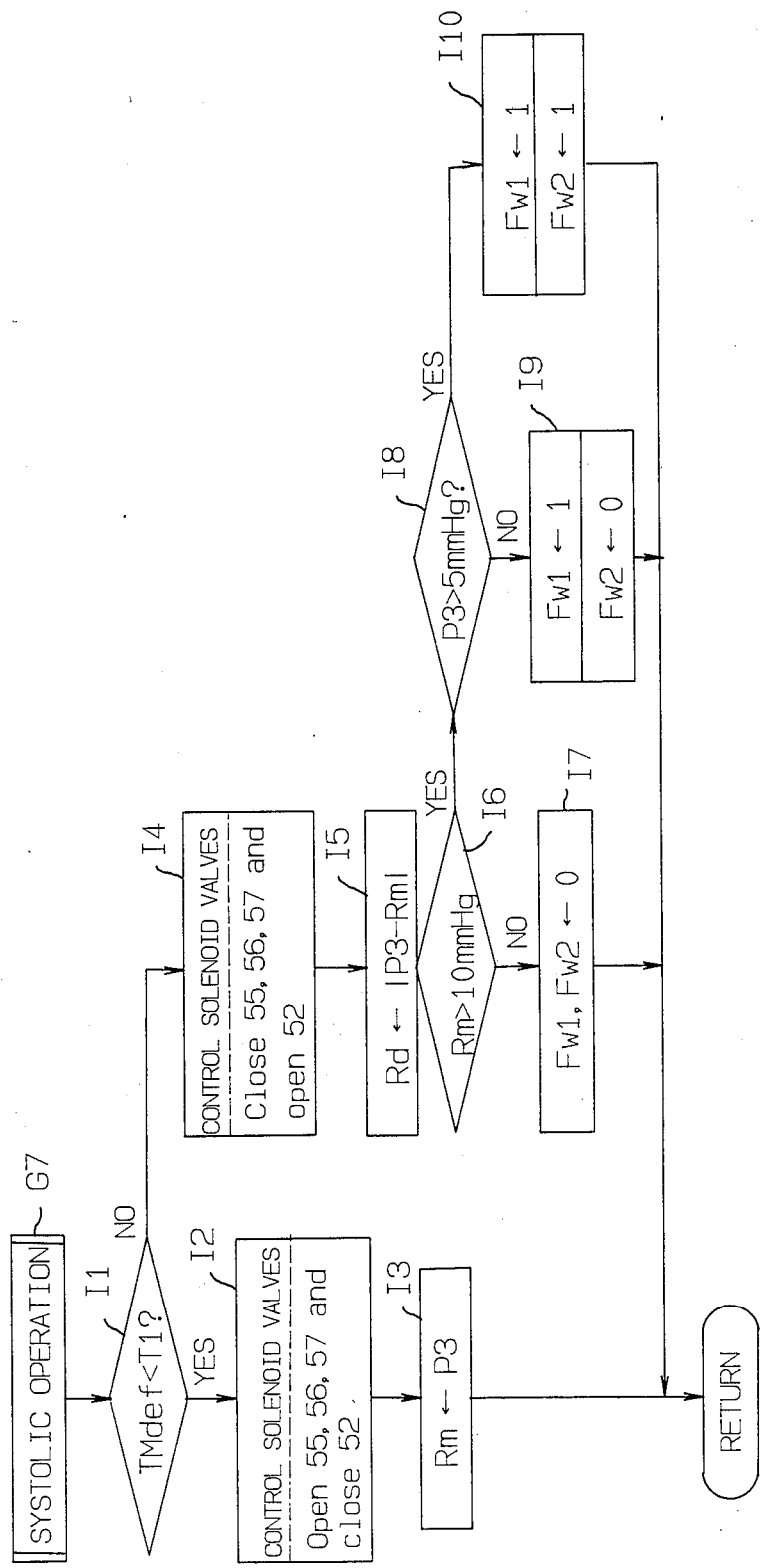

The detail of the diastolic subroutine is shown in FIG. 7h while the detail of the systolic subroutine is shown in FIG. 7i. Referring to FIG. 7h, the diastolic subroutine will be described first. In this subroutine, the content of the timer TMinf is initially examined. If TMinf>T1, indicating that the time duration of the diastole of the balloon pump is less than T1, the program proceeds to a step H2 where the solenoid valves 52, 56 and 57 are set to be open while the solenoid valve 55 is set to be closed. This causes the positive pressure within the accumulator AC1 to be applied to the balloon pump 60B through the valve 52, the isolator AGA and the valves 56, 57, whereby th balloon pump 60B assumes its diastolic phase. A sample of the signal delivered by the pressure sensor P3 is then stored in a register Rm while a sample of the signal delivered by the pressure sensor P2 is stored in the register Rphe. The content of the register Rphe is referred to during the gas pressure control subroutine. When the time passes and the inequality TMinf≧T1 applies, indicating that the time duration of the diastole of the balloon pump has exceeded T1, the program proceeds to a step H4 where the solenoid valves 52, 56 and 57 are set to be closed while the valve 55 is set to be open. A full inflation of the balloon pump is enabled when the given positive pressure is applied thereto during the time interval T1, and hence it maintains expanded condition if the solenoid valves 56 and 57 are subsequently closed. When the valve 56 is closed, this disconnects the balloon pump 60B from the channel 71 on the input side of the valve 56, whereby the balloon pump is allowed to maintain its inflated condition if the pressure within the channel 71 is switched to a negative pressure.

In the present example, the valves 52 and 55 are switched to change a portion of the flow path which is upstream of the channel 71 to a negative pressure substantially at the same time as the valves 56 and 57 are closed. This assures a sufficient length of time left until the initiation of the next systolic cycle during which the negative pressure in the drive unit may be stabilized sufficiently in preparation to the following systolic operation. However, it will be noted that there is a significant pressure differential between the inlet and the outlet of the valve 56. Accordingly, if the valve 56 is sealed imperfectly, there is a likelihood of a fluid leakage between the inlet and the outlet of the valve 56. To cater for this, the presence or absence of such fluid leakage is determined by detecting a change in the pressure with the pressure sensor PS4 which is disposed in the flow path between the valves 56 and 57. Specifically, at step H5, a difference between the pressure P3 detected at this time by the pressure sensor PS4 and the pressure stored in the register Rm is stored in a register Rd, which is then referred to at subsequent steps H6 and H8 to determine the presence or absence of any abnormality.

Specifically, in the present example, when the content of the register Rd exceeds 10 mmHg, a flag Fwl is set to "1", and when the content exceeds 20 mmHg, another flag Fw2 is set to "1". When the flag Fwl is set to "1", the microcomputer 100 delivers a given display command to the operating board control unit 300 to cause the display on the operating board 100 to indicate "the occurrence of a fluid leakage" (not shown). When the flag Fw2 is set to "1", the microcomputer 100 determines that a serious abnormality has occurred, and operates to energize the buzzer 195 at a step A8 shown in FIG. 7a.

The content of the register Rm is continually updated with a reduced period when the timer TMinf is less than T1, so that during the execution of the step H5, the content of the register Rm represents the pressure (P3) which is sampled immediately before the value in the timer TMinf assumes T1.

It is to be understood that the described unit operates in a normal manner in the absence of the solenoid valve 57, the provision of which is however desirable for the following reasons:

(a) In the event a fluid leakage occurs through the solenoid valve 56, the provision of the solenoid valve 57 prevents any resulting change in the pressure from being transmitted to the balloon pump 60B, thus assuring the safety of operation. When a fluid leakage occurs through the valve 56, a pressure differential across the inlet and the outlet of the valve 57 is small, which means that the likelihood that a fluid leakage then develops through the both valves 56 and 57 is greatly reduced.

(b) The volume of a flow path between the valves 56 and 57 and in which the pressure sensor PS4 is disposed is reduced, and this causes a greater change in the pressure of the flow path in the event of occurrence of a fluid leakage, thus enhancing the sensitivity with which any abnormality can be detected.

Referring to FIG. 7i, the systolic subroutine will be described. In this subroutine, the content of the deflation timer TMdef is compared against T1. If TMdef<T1, indicating that the time duration after the balloon pump entered its systole is less than T1, the program proceeds to a step I2 where the valves 55, 56 and 57 are set to be open while the valve 52 is set to be closed. This causes the negative pressure within the accumulator AC2 to be applied to the balloon pump 60B through the valve 55, isolator AGA and valves 56 and 57, thus causing the balloon pump 60B to assume a deflating condition. A signal delivered by the pressure sensor PS4 is sampled, and the sample is stored in the register Rm.

When the inequality TMdef≧T1 applies, indicating that the time duration of the balloon pump in its systole is equal to or greater than T1, the program proceeds to a step I4 where the valves 55, 56 and 57 are set to be closed while the valve 52 is set to be open. When the given negative pressure is applied to the balloon pump for the time interval T1, it is deflated fully and maintains its deflated condition if the valves 56 and 57 are then set to be closed. When the valve 56 is closed, this results in a separation of the balloon pump 60B from the channel 71 on the input side of the valve 56, and accordingly if the pressure within the channel 71 is switched to a positive one, the balloon pump is maintained in its systolic condition. As during the inflation, the valves 52 and 55 are switched to change the flow path upstream of the channel 71 to a positive pressure substantially simultaneously with closing the valves 56 and 57, generally in the similar manner as before. This provides a sufficient time margin until the initiation of the next diastolic operation during which the positive pressure within the drive unit may be sufficiently stabilized in preparation for the next diastolic operation.

As before, the likelihood of a fluid leakage occurring through the solenoid valve 56 is determined by utilizing the pressure sensor PS4 which detects a change in the pressure. Specifically, at step I5, a difference between the prevailing pressure P3 detected by the sensor PS4 and the pressure which is stored in the register Rm is stored in a register Rd, the content of which is referred to at steps I6 and I8 to determine the presence or absence of any abnormality. Specifically, in the present example, when the content of the register Rd exceeds 10 mmHg, the flag Fw1 is set to "1", and when the presence P3 exceeds 5 mmHg, the flag Fw2 is set to "1".

The attention of the reader is directed to FIG. 8a which indicates the operation of various parts of the unit and the timing of various signals during the balloon control.

During the communication subroutine shown by step A6 in FIG. 7a, information relating to the pressures detected and the presence or absence of any abnormality is communicated to the microcomputer 310 within the operating board control unit 300.

Figure 9A:
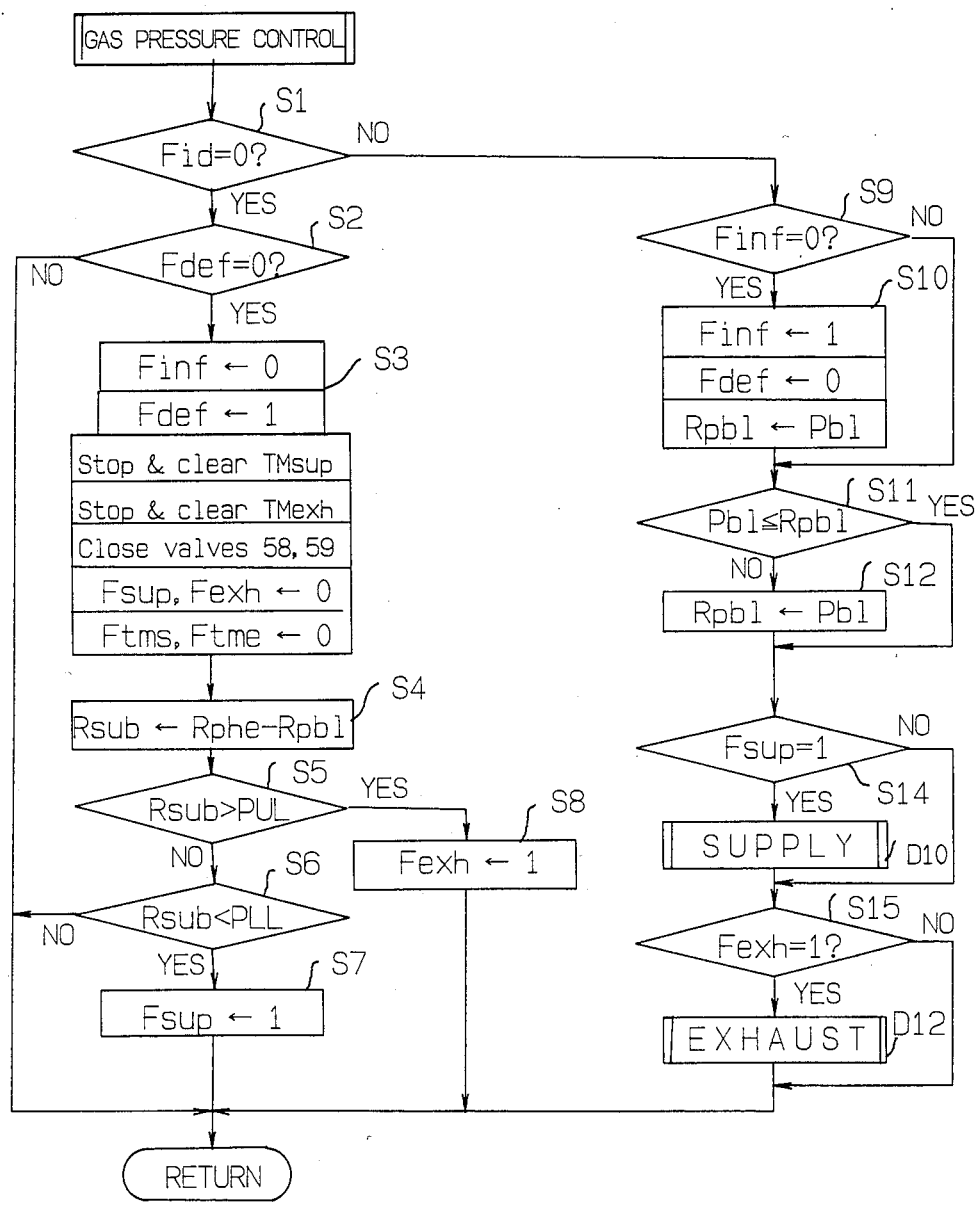
FIG. 9a is a flowchart of another embodiment of the invention.

FIGS. 9a and 9b illustrate a modification of the gas pressure control. In this modification, the arrangement of the unit as well as the operation of components not related to the gas pressure control remain the same as before. Briefly describing the modification, a blood pressure which is delivered by the hemadynamometer 140 is utilized as one of the parameters which control the solenoid valves 58 and 59, in addition to the pressure P2 delivered by the sensor PS3. Thus, in this modification, a maximum value of the blood pressure Pbl during the diastole is stored in a register Rpbl, and immediately after a change from the diastolic to the systolic period, a difference between the content of register Rphe and register Rpbl is stored in a register Rsub, the content of which is then compared against an upper limit PUL and the lower limit PLL. An exhaust flag Fexh and an air supply flag Fsup are set or reset in accordance with the result of such comparison. In this manner, in this modification, the quantity of gas on the secondary side of the isolator is regulated so as to maintain a difference between the driving pressure of the balloon pump and the blood pressure of the physical body within a given range.

As described, in accordance with the invention, a pressure regulation takes place automatically for balloon pumps of different capacities, thus dispensing with a regulating operation on the part of the operator. In addition, the use of a hose of an arbitral length with unknown volume of flow path for driving the balloon pump is permitted. A constraint on the movement of the diaphragm of the isolator is eliminated, allowing a greater negative pressure (in absolute value) to be applied to the balloon pump to reduce the length of time which is required for the deflating operation.

I claim:

1. A drive unit for medical pump comprising
   pressure producing means for producing a driving pressure in the form of an alternating positive and negative pressure;
   fluid isolator means having its interior divided into a primary and a secondary side, with the primary side being connected to the output of said pressure producing means;
   connection means internally containing a fluid passage for connecting the secondary side of the fluid isolator means to a medical pump;
   first valve means for supplying a given fluid to the interior of the connection means;

second valve means for exhausting the fluid within the connection means to the exterior thereof;

first pressure detecting means responsive to the pressure within the connection means to produce a corresponding electrical signal and electronic control means connected to said first and second valve means and said first pressure detecting means for monitoring the electrical signal developed by the first pressure detecting means when said pressure producing means produces a positive pressure to thereby determine the pressure within the connection means and for controlling flow of fluid through the first and the second valve means in accordance with the pressure thus determined to control the pressure within said connection means.

2. A drive unit for medical pump according to claim 1 in which the electronic control means periodically and repeatedly samples the electrical signal developed by the first pressure detecting means as said means produces a positive pressure, determines the pressure which prevails within the connection means based on the last sample of the electrical signal as the pressure produced by said means changes to a negative pressure, controls the first and the second valve means to be closed when the pressure determined lies in a range defined by a given upper limit and lower limit, controls the second valve means to be open at least during a given time interval when said pressure determined exceeds the upper limit while the control means controls the first valve means to be open at least during a given time interval when the pressure determined is less than the lower limit.

3. A drive unit for medical pump according to claim 1 in which said electronic control means is provided with blood pressure detecting means which detects the blood pressure of a physical body in which the medical pump is mounted, the control means operating to determine the maximum value of blood pressure delivered by the blood pressure detecting means as said means produces a positive pressure and to control the first and the second valve means in accordance with a difference between the maximum value of the blood pressure and the pressure delivered by the first pressure detecting means.

4. A drive unit for medical pump according to claim 1 in which the electronic control means is provided with blood pressure detecting means which detects the blood pressure of a physical body in which the medical pump is mounted, the electronic control means operating to determine the maximum value of the blood pressure which is output from the blood pressure detecting means as said means produces a positive pressure, to sample the electrical signal which is output from the first pressure detecting means periodically and repeatedly, to determine the pressure which prevails within the connection means on the basis of the last sample of the electrical signal when the pressure produced by said means changes to a negative pressure, to control the first and the second valve means to be closed if a difference between the pressure which prevails within the connection means and a maximum value of the blood pressure lies in a range defined by a given upper and lower limit, and to control the first valve means to be open at least during a given time interval if the difference is above the upper limit, and to control the second valve means to be open at least during a given time interval if the difference is below the lower limit.

5. A drive unit for medical pump according to claim 1 in which said connection means is provided with third valve means interposed in a flow path extending between the secondary side of the fluid isolator and the medical pump, the electronic control means operatively connected with said pressure producing means and said third valve means to open the third valve means during a given time interval to apply the pressure in the connection means to the medical pump and to close the third valve means after the given time interval has passed and control said pressure producing means to switch the pressure applied to the primary side of the fluid isolator from one of said positive and negative pressures to the other of said positive and negative pressures to thereby switch the pressure in the secondary side of said fluid isolator and said connection means.

6. A drive unit for medical pump according to claim 5 in which said connection means is provided with fourth valve means interposed in a flow path extending between the third valve means and the medical pump, and second pressure detecting means connected to said control means and interposed in a flow path extending between the third and the fourth valve means to provide an electrical signal, the electronic control means operating to open the third and the fourth valve means only during said given time interval and monitoring the electrical signal which is output from the second pressure detecting means when the third and the fourth valve means are closed to determine the presence or absence of any abnormality in the pressure, the control means annunciating the occurrence of an abnormality upon detection of an abnormality in the pressure.

7. A drive unit for medical pump according to claim 1 in which the medical pump is a balloon pump placed within the aorta.

* * * * *